(12) United States Patent
Norton

(10) Patent No.: US 8,883,222 B2
(45) Date of Patent: Nov. 11, 2014

(54) DISINFECTANT MATERIALS AND METHODS

(75) Inventor: David Norton, Dorset (GB)

(73) Assignee: Mauve Technology Limited, Wimborne, Dorset (GB)

( * ) Notice: Subject to any disclaimer, the term of this patent is extended or adjusted under 35 U.S.C. 154(b) by 3 days.

(21) Appl. No.: 13/576,224

(22) PCT Filed: Feb. 3, 2011

(86) PCT No.: PCT/GB2011/050180
§ 371 (c)(1),
(2), (4) Date: Jul. 31, 2012

(87) PCT Pub. No.: WO2011/095809
PCT Pub. Date: Aug. 11, 2011

(65) Prior Publication Data
US 2012/0301556 A1 Nov. 29, 2012

(30) Foreign Application Priority Data

Feb. 3, 2010 (GB) .................. 1001717.6
Dec. 9, 2010 (GB) .................. 1020901.3

(51) Int. Cl.
*A61K 33/14* (2006.01)
*A01N 59/06* (2006.01)
*A01N 59/00* (2006.01)
*A61K 33/20* (2006.01)
*A01N 59/08* (2006.01)

(52) U.S. Cl.
CPC .............. *A01N 59/08* (2013.01); *A01N 59/06* (2013.01); *A01N 59/00* (2013.01); *A61K 33/20* (2013.01)
USPC ...................................... 424/661

(58) Field of Classification Search
CPC .................................................... A61K 33/20
See application file for complete search history.

(56) References Cited

U.S. PATENT DOCUMENTS

| 6,258,249 B1 | 7/2001 | Simpson |
| 2009/0016990 A1 | 1/2009 | Alberte et al. |

FOREIGN PATENT DOCUMENTS

| CA | 2 028 930 | 5/1992 | | |
| GB | 2422545 | 8/2006 | | |
| GB | 2437489 A | * 10/2007 | ............. | A01N 59/00 |
| JP | 57111363 A | * 7/1982 | ............... | C09D 9/00 |
| JP | 2001 259652 | 9/2001 | | |
| JP | 2008 036020 | 2/2008 | | |
| KR | 2001 044 875 | 11/1999 | | |
| WO | 98/21308 A2 | 5/1998 | | |
| WO | 00/51434 A1 | 9/2000 | | |
| WO | 2005/089100 A2 | 9/2005 | | |
| WO | 2008/116509 A1 | 10/2008 | | |

* cited by examiner

*Primary Examiner* — Lezah Roberts
*Assistant Examiner* — Nannette Holloman
(74) *Attorney, Agent, or Firm* — Larson & Anderson, LLC

(57) ABSTRACT

A disinfectant combination comprises a first supply of a water-soluble hypochlorite; and a second supply of at least one saturated, water-soluble, physiologically acceptable carboxylic acid in solution in an alcoholic solvent which comprises ethanol and optionally water. The combination is used in a method of disinfection, in which a dosed amount of the first supply is mixed with a dosed amount of the second supply to form a disinfectant in situ, and the resulting combined solution, optionally diluted with further water, is applied to a surface or article to be disinfected. In a preferred embodiment, the combination is used for disinfection of endoscopes.

6 Claims, No Drawings

DISINFECTANT MATERIALS AND METHODS

This application is the US national stage of PCT/GB2011/050180 filed 3 Feb. 2011, which claims priority to GB1001717.6 filed on 3 Feb. 2010 and GB1020901.3 filed on 9 Dec. 2010 (now GB Patent 2477597), which are incorporated by reference.

The present invention is concerned with disinfectant materials and with methods of disinfecting.

Chlorine and chlorine-based disinfectants have been widely used in the medical field as early as the 18th century. Chlorine-based chemicals, such as sodium hypochlorite, have also been used for many years in water and sewage treatment, and for sterilising equipment subject to contamination. Other chlorine donors, such as calcium hypochlorite, have also been used as disinfectants or sterilising agents. Several bacteriological studies have demonstrated that the effectiveness and efficacy of such hypochlorites depends chiefly on the concentration of hypochlorous acid present in solution when the chemicals are put into use.

The concentration of hypochlorous acid depends on the amount and concentration of the hypochlorite, and also on the pH of the solution. Specifically, the more alkaline the solution, the less hypochlorous acid is present, and consequently the less effective the solution is as a disinfectant or sterilant. At near neutral pH (such as pH 7.5) only 50% of the chlorine is present as hypochlorous acid (HOCl) and the remaining is present as hypochlorite ions (OCl$^-$). As the pH of the solution increases further (to a pH of greater than 7.5), the relative concentration of hypochlorite ions increases, relative to hypochlorous acid content and the germicidal efficacy decreases still further.

On the other hand, as the solution is acidified to a pH of less than 7.5, the relative concentration of hypochlorous acid increases and the germicidal efficacy increases significantly. At a pH of 6.5, approximately 90% of the chlorine will be available as hypochlorous acid. It is in the pH range of 5 to 6 that such solutions are at their most potent because at these pH values, hypochlorous acid provides greater than 98% of the free available chlorine.

Hypochlorous acid is known to be highly active against a range of pathogens such as *Mycobacterium tuberculosis, Mycobacterium avium intracellulare, Mycobacterium chelonae*, methicillin-resistant *Staphylococcus aureus, Candida albicans, Escherichia coli, Pseudomonas aeruginosa, Enterococcus faecalis, Bacillus subtilis* and human immunodeficiency virus HIV-1.

Accordingly, it could be expected that hypochlorites would be widely used, particularly in the medical field, as potent germicides. However, this is not currently the case because their solutions are generally commercially available only at relatively high pH values, which in turn is because they are only adequately stable in alkaline conditions. However, although stable, they are not very effective as disinfecting or sterilising solutions at such high pH values. Also, at these relatively high pH values the solutions cause significant skin irritation and corrosion of equipment.

Hypochlorites at their most potent pH (pH 5 to 7 or slightly acidic) have a very short life cycle (usually a few days at most) and consequently cannot be stored for extended time periods.

GB2437489 discloses the use of at least one of sodium hypochlorite (NaOCl) and calcium hypochlorite [Ca(OCl)$_2$] as a chlorine donor together with one or more acids, such as dicarboxylic or tricarboxylic acids, for example, oxalic acid, malonic acid, succinic acid, glutaric acid, adipic acid, pimelic acid, suberic acid, and citric acid. The hypochlorite and the acids can be provided in solid (typically powdered or granular) form to be made up in water when required, or stored in aqueous solution.

While such an aqueous solution has reasonable storage stability, deterioration over time is inevitable. For maximum efficacy, therefore, the disinfectant solution may be made up shortly before use by mixing together separate supplies of the hypochlorite and the acid.

For example, WO00/51434 discloses a weak acid disinfectant comprising a first agent (which may contain e.g. sodium or calcium hypochlorite) and a second agent (which may contain e.g. succinic acid). The two agents may be packaged separately, or composed into one package. The disinfectant is provided in the form of an aqueous solution.

CA2028930 discloses a method of providing a hypochlorous acid sterilant solution by combining a first solution containing a hypochlorite salt with a second component that may be e.g. acetic acid or formic acid.

WO98/21308 discloses an acid bleaching composition prepared from a first aqueous containing succinic acid and a second aqueous solution containing hypochlorite.

However, when separate solutions of hypochlorite and acids are used, it can frequently be difficult to ensure complete dissolution.

According to the invention therefore, there is provided a disinfectant combination, which comprises;
  (a) a first supply of a water-soluble hypochlorite, the hypochlorite being preferably in aqueous solution;
  (b) a second supply of at least one saturated, water-soluble, physiologically acceptable carboxylic acid;
    in which the carboxylic acid is in solution in an alcoholic solvent which comprises ethanol and optionally water.

The ethanol acts as an effective solvent for the carboxylic acid and allows the two supplies to be provided as separate liquid concentrates, which are to be mixed together in water before the combination is used as a disinfectant. The materials used in the disinfectant system are simple to use by untrained personnel and do not necessitate the use of special equipment; they are environmentally friendly and do not necessitate special ventilation or disposal equipment. Each of the two components may be easy to package and distribute, with good storage stability and a long shelf life.

GB 2422545 discloses a dispenser for a two part disinfectant solution. one part being typically hypochlorite and the other part being typically an acid solution. The document discloses that the two parts are combined and dispensed in the form of a foam The document further discloses that either or both parts may contain other 'solvents' such as ethanol or glycerol (provided that a sufficiently stable foam can be achieved. There is no hint or suggestion that an acid should be pre-dissolved in alcoholic solvent that comprises ethanol and optionally water, and consequently no hint or suggestion of advantages stemming from the use of the acid in solution in such an alcoholic solvent.

The hypochlorite used in the combination according to the present invention may be in dry form, to be mixed for use in water, with the carboxylic acid in solution in the alcoholic solvent.

Surprisingly, it has also been found that the use of a disinfectant combination according to the present invention may cause less damage to medical apparatus, such as endoscopes, than conventional disinfectants. Effectively, the lifetime of the apparatus such as endoscopes may be significantly increased, since they have been found to be able to withstand a greater number of disinfection cycles using the combination according to the invention.

Traditionally, glutaraldehyde has been the most commonly used disinfectant in endoscopy units, because it is relatively inexpensive, and does not damage endoscopes, accessories or automated processing equipment. However, glutaraldehyde is asthamagenic, and adverse reactions to glutaraldehyde are common among endoscopy personnel. The use of glutaraldehyde has therefore been significantly curtailed (and in some countries glutaraldehyde has been withdrawn from use for this reason). Various alternative disinfectants have therefore been proposed for endoscopes, such as ortho-phthalaldehyde, succinic dialdehyde, peracetic acid and chlorine-containing disinfectants. Chlorine-containing disinfectants are known to cause damage to the lacquer coating of some endoscopes, and therefore have not hitherto been considered to be entirely satisfactory for this purpose.

It is therefore surprising that endoscopes can be disinfected 50 to 100 times using the combination according to the invention, while maintaining the lacquer in pristine, undamaged condition.

The carboxylic acid used in the combination according to the invention may be mono-, di- or tri-functional; it is preferably a saturated (alkanoic) acid. Optionally, the acid may have one or more substituents which are substantially inert in the presence of a chlorine donor. The acid is preferably a solid (when in pure, isolated form at 20° C., although of course according to the invention, the acid is provided in alcoholic solution). The acid is typically an alkane dioic acid with up to 7 carbon atoms in a saturated chain, or a hydroxyl substituted acid such as citric acid. As the length of the carbon chain increases, the solubility of the acid in water and alcohol decreases, so the carbon chain length should not be such that the acid is no longer soluble in the alcoholic solvent.

Typical such carboxylic acids for use according to the invention include one or more of oxalic acid, malonic acid, succinic acid, glutaric acid, adipic acid, pimelic acid and suberic acid. An especially preferred such acid is adipic acid.

The alcoholic solvent for the carboxylic acid preferably comprises 40 to 60% by weight of ethanol, with substantially all the balance being water. It is particularly preferred that the solvent consists of substantially equal amounts by weight of ethanol and water (that is, each is preferably present in an amount of 45 to 55% by weight). It is possible to use pure ethanol as the alcoholic solvent, but more usually an Industrial denatured alcohol or a trade specific denatured alcohol will be used. These are 99.9% pure ethanol and they are regularly used in the preparation of medical biocidal reagents and external medical applications such as creams and ointments.

The hypochlorite used in the first supply may be sodium hypochlorite and/or calcium hypochlorite. The first supply may be in the form of a sealed or closed pack containing the hypochlorite in aqueous solution, typically at an (alkaline) pH such that the solution has prolonged storage life. When in the form of a closed pack, the latter may be provided as a unit dose of hypochlorite solution, or a dispenser arranged to dispense predetermined amounts of the hypochlorite solution.

The preferred amount of hypochlorite such as calcium hypochlorite [$Ca(OCl)_2$] depends on the end use of the combination according to the invention. For example, for a free available chlorine content of 250 mg/l, approximately 300 mg of calcium hypochlorite [$Ca(OCl)_2$] would be required per liter of aqueous solution. For a free available chlorine level of 50 mg/l, approximately 60 mg of calcium hypochlorite [$Ca(OCl)_2$] would be required per liter of aqueous solution.

In either case, an equivalent amount of an acid such as adipic acid and/or succinic acid is required to obtain the necessary pH and subsequent efficacy. The former concentration [250 mg/l] is strong enough for disinfection and sterilisation of medical devices, for example, flexible endoscopes, orthopaedic instruments and the like. It is also suitable for use in complete room remediation and the removal of biofilms from water lines, for example, in dental units.

Typically the hypochlorite solution contains about 30 to 40 grams of hypochlorite per liter of water.

The aqueous solvent for the hypochlorite may, for example, be of potable tap water, deionised water or distilled water.

The second supply employed in the combination according to the invention may be in the form of a sealed or closed pack containing the carboxylic acid in solution in the ethanolic solvent. When in the form of a closed pack, the latter may be provided as a unit dose of carboxylic acid solution, or a dispenser arranged to dispense predetermined amounts of the solution of the carboxylic acid. Typically the carboxylic acid solution contains about 30 to 40 grams of acid per liter of 50/50 ethanol/water.

The first and second supplies may be in the form of separate containers (such as sachets or vials each containing the desired amount of the required ingredients); alternatively, a duplex container may be provided such that both can be opened simultaneously when it is desired to dispense the respective contents.

Both the hypochlorite solution and the carboxylic acid solution may contain acceptable non-deleterious additives, such as buffers, detergents or the like. When the carboxylic acid solution contains water, the latter may, for example, be .potable tap water, de-ionised water or distilled water. By "acceptable" we mean herein physiologically acceptable when the solutions are to be used to disinfect articles or surfaces intended to contact a human or animal body.

The combination according to the invention is preferably employed in a method of disinfection, in which a disinfectant is formed in situ. The method comprises dissolving at least one saturated, water-soluble, physiologically acceptable carboxylic acid, in an alcoholic solvent which comprises ethanol, the solvent optionally also containing water, and mixing the resulting solution with a dosed amount of a water-soluble hypochlorite (typically in aqueous solution). The mixture of the alcoholic solution and the hypochlorite are preferably diluted in water (typically using water in an amount of at least 20 times the volume of the concentrates).

The present invention further comprises a method of disinfecting a body of water, which comprises dissolving at least one saturated, water-soluble, physiologically acceptable carboxylic acid, in an alcoholic solvent which comprises ethanol, the solvent optionally also containing water, and mixing the solution with a dosed amount of a water-soluble hypochlorite in the body of water.

The body of water in the method of disinfection may, for example, be in a container such as a barrel, drum, bottle or the like, or it may be in the form of an open body such as a well, pool, or water course, or water in a pipeline. By this means, potable water may be obtained from a body of water which was previously unfit for consumption.

Preferably a dosed amount of the alcoholic solution is mixed with a dosed amount of the water-soluble hypochlorite, and the resulting combined solution, optionally diluted with further water, applied to a surface, material or article to be disinfected, or applied to the body of water. The diluted combined solution may be applied to the surface, material or article by spraying or by the use of an applicator, or by dipping, immersing or submerging the surface to be disinfected in the diluted combined solution.

It is particularly preferred to immerse an entire article to be disinfected in a reservoir containing a freshly prepared combined solution which has preferably been diluted with further water (again, typically of potable tap water, deionised water or distilled water).

The article to be disinfected may, for example, be an item for personal or medical use, such as an endoscopic device suitable for use in endoscopic inspection or surgery, typically using a disinfectant at solution strengths of about 200 to 300 ppm. The disinfection according to the invention may be carried out in automatic endoscopy reprocessing (AER) apparatus.

When used for this purpose, the disinfection cycle is preferably after a cleaning cycle (such as the manual removal of blood, secretions or other debris.

Disinfection according to the invention is then to substantially destroy vegetative microorganisms, mycobacteria, viruses, fungal spores and most bacterial spores to a level such that the disinfected article is suitable for safe use in a patient.

Other applications of the combination according to the invention include the disinfection of water lines, typically in dental surgeries so as to remove biofilm from within the lines, which could otherwise lead to cross contamination. Further applications are for a weaker solution (typically about 40 to 60 ppm) for general hospital ward and theatre hard surface cleaning. Still further applications include disinfection of surfaces in abattoirs and the like (where of course the level of destruction of microorganisms, viruses and the like is not as stringent as for apparatus such as endoscopes which come into intimate contact with vulnerable patients.

Even lower concentrations of the combination according to the invention, say, for example, around 5 mg/l free available chlorine, may be employed for supplying bacteria-free water to dental unit water lines and water for misting of comestible produce such as salad, vegetable and fruit products, to enhance the appearance and shelf life thereof, in supermarkets or the like. Approximately 6 mg of calcium hypochlorite [$Ca(OCl)_2$] would be required for each liter of aqueous solution for such an application.

In a typical mode of operation, dosed amounts (such as about 200 ml) of each supply, in the form of a concentrate, may be separately dispensed and mixed with typically 25 to 27 liters of water to create a disinfecting solution, typically of pH about 6.0. The disinfecting solution thus formed is applied to the surface to be disinfected as indicated above.

The final pH of the disinfecting solution and its free available chlorine level in the form of hypochlorous acid can be varied or controlled by selecting the amounts and ratios of the respective ingredients. Thus an optimum pH can be selected so as to maximise the concentration of free available chlorine in the form of hypochlorous acid.

Preferred features and aspects of the present invention will now be illustrated with reference to the following worked Examples, which are of course of an illustrative rather than limiting nature.

EXAMPLE 1

7.5 g of powdered calcium hypochlorite was dissolved in 200 ml of de-ionised water and 7.5 g of adipic acid was dissolved separately in 200 ml of 50/50 ethanol/deionised water. The two solutions were then mixed and diluted into 25 L [62.5 fold] in deionised water, which produced an active chlorine content of approx. 250 ppm at a pH of 6-7. The mixed solution was pumped into a suitably sized receptacle where an endoscopic inspection device was submerged therein for a period of 5 minutes, after which it was tested and found to be substantially free of surface microorganisms.

The solution was also tested in standard test EN 13727 under simulated Clean Conditions: 0.03% Bovine albumin (final concentration) and Dirty Conditions: 0.3% Bovine albumin (final concentration) plus 0.3% sheep erythrocytes. The EN 13727 test method involves mixing 1 ml of the test bacteria with 1 ml of interfering substance (0.3% or 3% albumin with 0.3% sheep erythrocytes), and then adding 8 ml of the test disinfectant. After the required contact time, 1 ml is removed to 9 ml of recovery broth (8 ml neutralizer and 1 ml water) for 5 minutes after which it is plated onto Tryptone Soya Agar to detect surviving test bacteria.

When tested in this manner under simulated clean conditions, the solution resulted in a 5 $\log_{10}$ reduction in under one minute, easily meeting the requirements of test EN 13727. A 5 $\log_{10}$ reduction in under 60 minutes was also achieved under simulated dirty conditions. The results of such tests, carried out in duplicate, are summarised in the following table.

| | | $\text{Log}_{10}$ | Mean $\log_{10}$ reduction | | | | | |
| | | initial | Clean conditions | | | Dirty conditions | | |
| Test organism | Contact time | count | Test 1 | Test 2 | Mean | Test 1 | Test 2 | Mean |
|---|---|---|---|---|---|---|---|---|
| Staphylococcus aureus | 1 min | 8.23 | >7.23 | >7.23 | >7.23 | 2.91 | 3.38 | 3.15 |
| | 2 min | | >7.23 | >7.23 | >7.23 | 3.35 | 3.75 | 3.55 |
| | 5 min | | >7.23 | >7.23 | >7.23 | 3.35 | 3.85 | 3.60 |
| | 60 min | | >7.23 | >7.23 | >7.23 | >7.23 | >7.23 | >7.23 |
| Pseudomonas aeruginosa | 1 min | 7.69 | >6.69 | >6.69 | >6.69 | 3.21 | 3.43 | 3.32 |
| | 2 min | | >6.69 | >6.69 | >6.69 | 4.31 | 4.90 | 4.61 |
| | 5 min | | >6.69 | >6.69 | >6.69 | 4.39 | 4.61 | 4.50 |
| | 60 min | | >6.69 | >6.69 | >6.69 | >6.69 | >6.69 | >6.69 |
| Enterococcus hirae | 1 min | 7.65 | >6.65 | 6.16 | >6.41 | 2.86 | 2.61 | 2.74 |
| | 2 min | | >6.65 | >6.65 | >6.65 | 3.02 | 3.31 | 3.17 |
| | 5 min | | >6.65 | >6.65 | >6.65 | 2.61 | 3.22 | 2.92 |
| | 60 min | | >6.65 | >6.65 | >6.65 | >6.65 | >6.65 | >6.65 |

Similar results for clean conditions were also achieved in other tests relevant to chemical disinfectants in relation to the European Standards for chemical disinfectants [EN14885]. These are as follows Tuberculoidal Efficacy Tests EN14348, and Assessment of Sporicidal Activity & Virucidal Efficacy of a disinfectant using EN 14476.

EXAMPLE 2

Example 1 was repeated with a similar amount of succinic acid instead of adipic acid. Similar results were obtained.

EXAMPLE 3

7.5 g of powdered calcium hypochlorite was dissolved in 200 ml of deionised water. Separately, 3.75 g of adipic acid was mixed with 3.75 g of succinic acid and dissolved in 200 ml of 50/50 ethanol/deionised water. The two solutions were then mixed and further diluted into 25 L [62.5 fold] of deionised water which produced an active chlorine content of approx. 250 ppm at a pH of 6-7.

The mix was pumped into a suitably sized receptacle where an endoscopic inspection device was submerged therein for a period of 5 minutes, after which it was tested and found to be substantially free of surface microorganisms.

EXAMPLE 4

1.5 g of powdered calcium hypochlorite was dissolved in 100 ml of de-ionised water and 1.5 g of adipic acid was dissolved separately in 100 ml of 50/50 ethanol/deionised water. The two solutions were then mixed & diluted into 25 L [125 fold] in sealed container. This solution was then used to clean a laboratory hard-surface, after which the surface was immediately tested and found to be substantially free of surface microorganisms.

EXAMPLE 5

Example 4 was repeated with a similar amount of succinic acid instead of adipic acid. Similar results were obtained.

EXAMPLE 6

1.5 g of powdered calcium hypochlorite was dissolved in 100 ml of de-ionised water. Separately, 0.75 g of adipic acid was mixed with 0.75 g of succinic acid and dissolved in 100 ml of 50/50 ethanol/deionised water. The two solutions were then mixed and diluted into 25 L [125 fold] in a sealed container. This solution was then used to clean a laboratory hard-surface, after which it was immediately tested and found to be substantially free of surface microorganisms.

EXAMPLE 7

A mixed solution as made up in Example 1 was used to disinfect a range of cleaned endoscopes in an Automated Endoscope Reprocessing apparatus in an accelerated 300 cycle test (equivalent to 12 months normal usage). All endoscopes were examined pre- and post-disinfection; no corrosion, build or cracks were observed, and exposed metal parts were unaffected. The disinfection method therefore provides a significant advantage relative to prior art techniques, where damage is frequently noted.

The invention claimed is:

1. A disinfectant combination, which comprises;
    a first supply of a water-soluble hypochlorite; and
    a second supply of at least one saturated, water-soluble, physiologically acceptable carboxylic acid, wherein the carboxylic acid is in solution in an alcoholic solvent which comprises 40 to 60% by weight of ethanol, substantially all the balance of the solvent being water.

2. A combination according to claim 1, wherein the hypochlorite is in aqueous solution.

3. A combination according to claim 1, wherein the carboxylic acid is a mono-, di- or tri-functional, saturated alkanoic acid.

4. A combination according to claim 3, wherein the acid is a solid when in pure isolated form at 20° C., and is an alkane dioic acid with up to 7 carbon atoms in a saturated chain, or a hydroxyl substituted alkanoic acid.

5. A combination according to claim 1, wherein the first supply is in the form of a sealed or closed pack containing the hypochlorite in aqueous solution at an alkaline pH.

6. A combination according to claim 1, wherein the second supply is in the form of a further sealed or closed pack containing the carboxylic acid in solution in said alcoholic solvent.

* * * * *